(12) United States Patent
Balda et al.

(10) Patent No.: US 9,498,145 B2
(45) Date of Patent: *Nov. 22, 2016

(54) CARDIAC EVENT MONITORING SYSTEM

(71) Applicant: MEDICOMP, INC., Melbourne, FL (US)

(72) Inventors: Daniel Balda, Indian Harbour Beach, FL (US); Robert Michael Thomas, Indian Harbour Beach, FL (US); Monte Marek, Palm Bay, FL (US); Tary Mann, Satellite Beach, FL (US); Anthony Balda, Satellite Beach, FL (US)

(73) Assignee: Medicomp, Inc., Melbourne, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/337,639

(22) Filed: Jul. 22, 2014

(65) Prior Publication Data

US 2014/0336491 A1    Nov. 13, 2014

Related U.S. Application Data

(63) Continuation of application No. 14/197,826, filed on Mar. 5, 2014, now Pat. No. 9,198,590, which is a continuation of application No. 11/550,759, filed on Oct. 18, 2006, now Pat. No. 8,983,583.

(51) Int. Cl.
*A61B 5/0408*   (2006.01)
*A61B 5/024*    (2006.01)
(Continued)

(52) U.S. Cl.
CPC ......... *A61B 5/0408* (2013.01); *A61B 5/02438* (2013.01); *A61B 5/0404* (2013.01); *A61B 5/0428* (2013.01); *A61B 5/0432* (2013.01); *A61B 5/04325* (2013.01); *A61B 5/6826* (2013.01); *A61B 2018/00178* (2013.01);
(Continued)

(58) Field of Classification Search
CPC .................................................... A61B 5/0404
See application file for complete search history.

(56) References Cited

U.S. PATENT DOCUMENTS

| 3,556,084 A | 1/1971 | Budde |
| 4,583,553 A | 4/1986 | Shah |

(Continued)

FOREIGN PATENT DOCUMENTS

| WO | WO 85-05547 | 12/1985 |
| WO | WO 2013-144968 A1 | 10/2013 |

OTHER PUBLICATIONS

Patient Instructions WristRecorder™ Plus, LifeWatch, (www.lifewatchinc.com), Feb. 2004, 8 pages.

(Continued)

*Primary Examiner* — Michael Kahelin
(74) *Attorney, Agent, or Firm* — Mark Malek; William Harding; Widerman Malek, PL

(57) ABSTRACT

A cardiac event monitoring system may include a base unit including a base connector, a wearable electrode system, and a plug-in adapter. The wearable electrode system includes a cable, an electrode at one end of the cable, and a cable connector at the other end of the cable. The cable connector is configured to plug into the base connector. The plug-in adapter includes electrodes and an adapter connector that is configured to plug into the base connector. A handheld device may include a plug-in adapter having first and second electrodes and a controller that is configured to process electrical signals detected by at least one of the first or second electrodes that are indicative of a cardiac event.

19 Claims, 6 Drawing Sheets

(51) Int. Cl.
*A61B 5/0404* (2006.01)
*A61B 18/00* (2006.01)
*A61B 5/0432* (2006.01)
*A61B 5/0428* (2006.01)
*A61B 5/00* (2006.01)

(52) U.S. Cl.
CPC ............ *A61B 2560/0209* (2013.01); *A61B 2560/0468* (2013.01); *A61B 2562/226* (2013.01)

(56) References Cited

U.S. PATENT DOCUMENTS

| | | | |
|---|---|---|---|
| 5,027,824 | A | 7/1991 | Dougherty et al. |
| 5,285,783 | A | 2/1994 | Secker |
| 5,316,008 | A | 5/1994 | Suga et al. |
| 6,032,060 | A | 2/2000 | Carim et al. |
| 6,366,871 | B1 | 4/2002 | Geva |
| 6,783,492 | B2 | 8/2004 | Dominguez et al. |
| 6,871,089 | B2 | 3/2005 | Korzinov et al. |
| 7,222,054 | B2 | 5/2007 | Geva |
| 2005/0143670 | A1* | 6/2005 | Umeda ............... A61B 5/0404 600/509 |
| 2005/0203349 | A1* | 9/2005 | Nanikashvili ........ A61B 5/0002 600/300 |
| 2007/0021676 | A1* | 1/2007 | Han .................... A61B 5/0452 600/509 |
| 2008/0097231 | A1 | 4/2008 | Balda et al. |
| 2014/0187898 | A1 | 7/2014 | Balda et al. |

OTHER PUBLICATIONS

Patient Instructions Micro ER, Life Watch, (www.lifewatchinc.com), prior to Oct. 18, 2006, 8 pages.
PCT International Search Report (Application No. PCT/US2007/081668) filed Oct. 17, 2007, mailed Apr. 7, 2008 (3 pages).
PCT Written Opinion (Application No. PCT/US2007/081668) filed Oct. 17, 2007, mailed Apr. 7, 2008 (7 pages).
ReadMyHeart V2.0, DailyCare BioMedical Inc., Taiwan, (www.debiomed.com), 2005, 49 pages.
HeartOne™, Pocketsize Transtelephonic ECG Event Recorder, HeartOne Aerotel Medical Systems, (http://www.aerotel.com/HeartOne.asp?id=65), prior to Oct. 18, 2006, 1 page.
Handheld ECG, ReadMyHeart, DailyCare Biomedical Inc., Taiwan, (www.debiomed.com), prior to Oct. 18, 2006, 2 pages.
CardioPAL™. . . Medicomp's Event Monitoring Solution, Medicomp, (www.medicompine.com), (1998), 2 pages.

* cited by examiner

CARDIAC EVENT MONITORING SYSTEM

RELATED APPLICATIONS

This application is a continuation and claims the benefit under 35 U.S.C. §120 of U.S. patent application Ser. No. 14/197,826, titled Cardiac Event Monitoring System filed by the inventor of the present application on Mar. 5, 2014, which, in turn, is a continuation and claims the benefit under 35 U.S.C. §120 of pending U.S. patent application Ser. No. 11/550,759, titled Cardiac Event Monitoring System filed by the inventor of the present application on Oct. 18, 2006, the entire contents of each of which are incorporated herein by reference.

FIELD OF THE INVENTION

The present invention relates to a cardiac event monitoring system.

BACKGROUND

Cardiac event monitoring is a procedure that is conducted on patients who report symptoms that may be cardiac in origin, and that occur infrequently, such as, for example, three times or less in one week. The term "event monitoring" is used because traditionally the test relied on the occurrence of symptoms, or "events." When symptoms occur, the patient activates an event monitor to record her electrocardiogram (ECG). The patient carries the event monitor during the testing period, which can last for several days or up to, for example, 30 days.

This background information is provided to reveal information believed by the applicant to be of possible relevance to the present invention. No admission is necessarily intended, nor should be construed, that any of the preceding information constitutes prior art against the present invention.

SUMMARY OF THE INVENTION

In one general aspect, a cardiac event monitoring system includes a base unit including a base connector, a wearable electrode system, and a plug-in adapter. The wearable electrode system includes a cable, an electrode at one end of the cable, and a cable connector at the other end of the cable. The cable connector is configured to plug into the base connector. The plug-in adapter includes electrodes and an adapter connector that is configured to plug into the base connector.

Implementations can include one or more of the following features. For example, the plug-in adapter can include two electrodes. The electrodes of the plug-in adapter can be each sized to receive a finger. The electrode of the wearable electrode system can be configured to be attached to a patient's skin. The electrodes of the plug-in adapter and the wearable electrode system can detect electrical signals from a patient's heart when coupled to the patient's skin.

The base unit can include a controller. The controller can be configured to operate in an auto capture mode, in manual mode, or in finger electrode mode. The base unit can include a speaker for transmitting data recorded from the plug-in adapter or the wearable electrode system. The base unit can include memory for storing data recorded from the plug-in adapter or the wearable electrode system. The base unit can include a display, and/or one or more input devices.

In another general aspect, a cardiac event monitoring system includes a base unit and a plug-in adapter. The base unit includes a base connector configured to receive a cable connector of a wearable electrode system. The plug-in adapter includes electrodes and an adapter connector configured to plug into the base connector of the base unit.

Implementations can include one or more of the following features. For example, the base unit can include a controller that is configured to operate in an auto capture mode.

Each of the electrodes can be sized to receive a finger. The electrodes of the plug-in adapter can detect electrical signals from a patient's heart when coupled to the patient's skin.

The base unit can include a speaker for transmitting data recorded from the plug-in adapter or the wearable electrode system. The base unit can include memory for storing data recorded from the plug-in adapter or the wearable electrode system.

In another general aspect, a method of monitoring cardiac events includes determining whether a wearable electrode system is connected to a base unit of a monitoring system, and if the wearable electrode system is connected to the base unit, operating the base unit to receive electrical signals from an electrode of the wearable electrode system. The method also includes determining whether a plug-in adapter is connected to the base unit if the wearable electrode system is not connected to the base unit, and operating the base unit to receive electrical signals from electrodes of the plug-in adapter if the plug-in adapter is connected to the base unit.

Implementations can include one or more of the following features. For example, the method can also include transmitting the electrical signals to a monitoring center if it is determined that the patient requested that the electrical signals be transmitted.

Operating the base unit to receive electrical signals from the electrode of the wearable electrode system can include monitoring the patient's electrical signals and recording the electrical signals if it is determined that the electrical signals are abnormal. Operating the base unit to receive electrical signals from the electrode of the plug-in adapter can include receiving an electrical signal from the electrode of the plug-in adapter when the patient puts a finger on at least one of the electrodes.

The method can include storing in memory electrical signals received from the plug-in adapter or the wearable electrode system for a predetermined time or until a patient transmits the electrical signals. The method can include displaying instructions to a patient on the base unit. The method can include receiving instructions from a patient from one or more input devices on the base unit.

In a further general aspect, a method of monitoring cardiac events includes providing a plug-in adapter that includes electrodes and an adapter connector that is configured to plug into a base connector of a base unit. The base connector is configured to receive a cable connector of a wearable electrode system that includes a cable, an electrode at one end of the cable, and the cable connector at the other end of the cable.

In another general aspect, a plug-in adapter includes a housing, two finger electrodes on one side of the housing, and an adapter connector on another side of the housing. The adapter connector is configured to plug into a connector of a base unit of a cardiac event monitor.

The cardiac event monitoring system provides a system that enables a patient to use a standard event monitor that uses wearable electrodes but also provides a patient with the option to use finger electrodes if the patient is uncomfortable with or does not want to use the wearable electrodes. The plug-in adapter is designed to be compatible with the base unit that is already designed to connect with the wearable electrode system. Therefore, the standard base unit does not need to be redesigned for use with the finger electrodes. It can be used for either the wearable electrodes or the finger electrodes, providing more options to the patient in a complete package.

Other features will be apparent from the description, the drawings, and the claims.

BRIEF DESCRIPTION OF THE DRAWINGS

Like reference symbols in the various drawings indicate like elements.

DETAILED DESCRIPTION OF THE INVENTION

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Those of ordinary skill in the art realize that the following descriptions of the embodiments of the present invention are illustrative and are not intended to be limiting in any way. Other embodiments of the present invention will readily suggest themselves to such skilled persons having the benefit of this disclosure. Like numbers refer to like elements throughout.

Although the following detailed description contains many specifics for the purposes of illustration, anyone of ordinary skill in the art will appreciate that many variations and alterations to the following details are within the scope of the invention. Accordingly, the following embodiments of the invention are set forth without any loss of generality to, and without imposing limitations upon, the claimed invention.

In this detailed description of the present invention, a person skilled in the art should note that directional terms, such as "above," "below," "upper," "lower," and other like terms are used for the convenience of the reader in reference to the drawings. Also, a person skilled in the art should notice this description may contain other terminology to convey position, orientation, and direction without departing from the principles of the present invention.

Furthermore, in this detailed description, a person skilled in the art should note that quantitative qualifying terms such as "generally," "substantially," "mostly," and other terms are used, in general, to mean that the referred to object, characteristic, or quality constitutes a majority of the subject of the reference. The meaning of any of these terms is dependent upon the context within which it is used, and the meaning may be expressly modified.

Cardiac event monitoring is used to evaluate a patient who experiences transient, infrequent symptoms of various forms of heart disease. Symptoms such as shortness of breath, dizziness, and palpitations are some of the common patient complaints. These symptoms may be caused by disturbances in the electrical signals that control the heart muscle contractions. The disturbances can be random, spontaneous, or emotion- or stress-induced.

Figure 1:
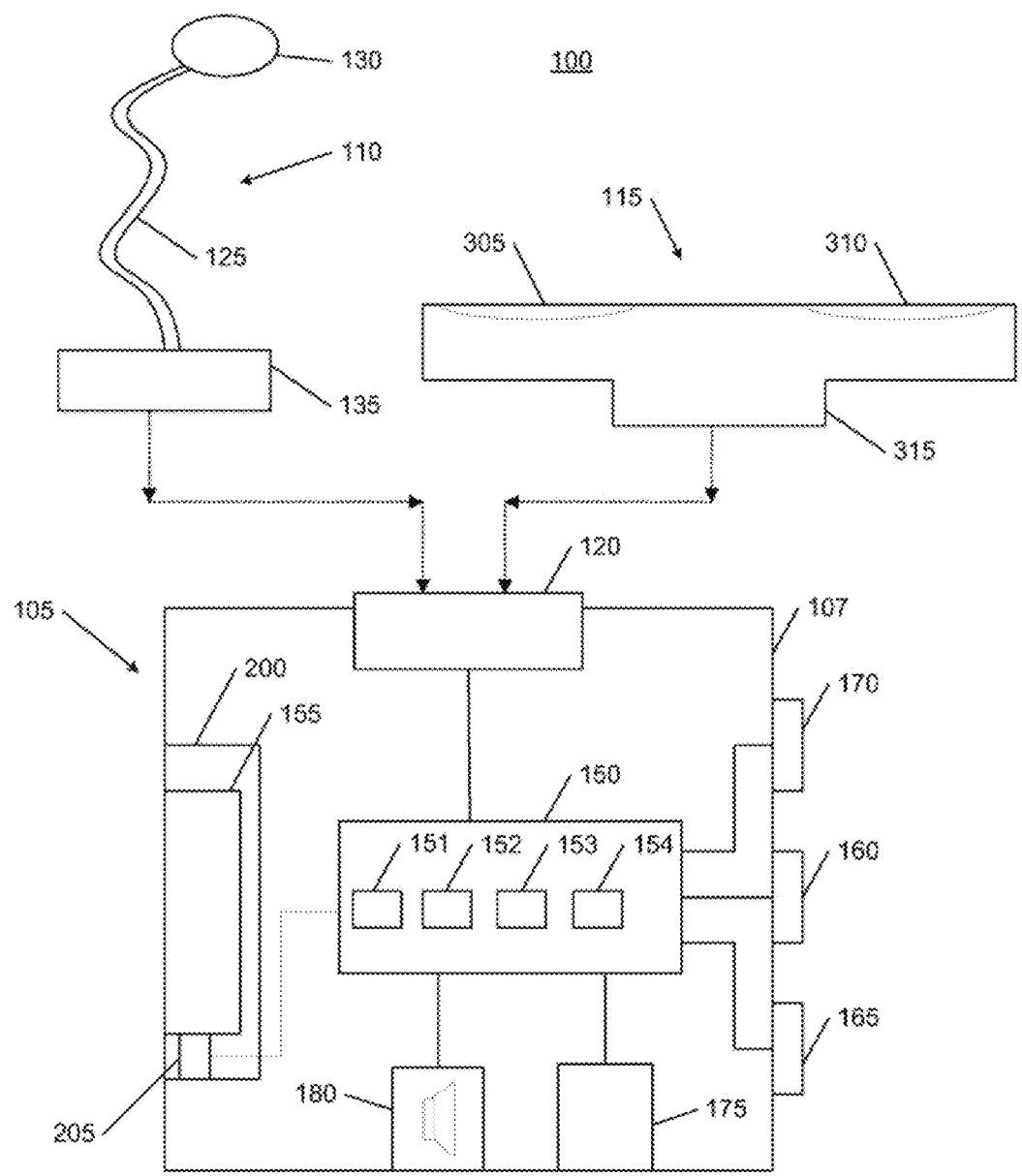
FIG. 1 is a block diagram of a cardiac event monitoring system.

Referring to FIG. 1, a cardiac event monitoring system 100 includes a base unit 105, a wearable electrode system 110, and a plug-in adapter 115. The base unit 105 includes a base connector 120 and a body 107 that houses the electrical components and includes a user interface, as discussed further below.

The wearable electrode system 110 includes a cable 125, at least two electrodes 130 at one end of the cable 125, and a cable connector 135 at the other end of the cable 125. The cable connector 135 is configured to plug into the base connector 120. Each electrode 130 is designed with a conducting member on a flat patch that contacts the patient's skin. In some cases, the flat patch of each electrode 130 is coated with a gel that improves electrical conduction between the patient's skin and the electrode surface. The patch can include an adhesive that sticks to the patient's skin. The electrodes 130 are usually placed along the patient's chest, at appropriate locations for producing the best ECG signal.

Figure 2A:
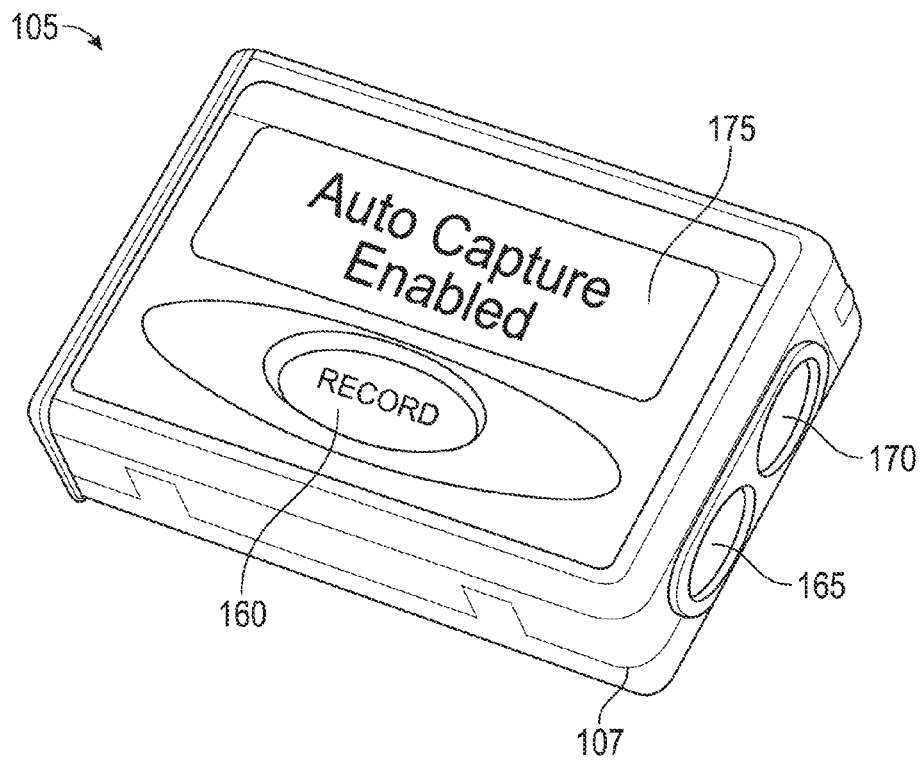
FIGS. 2A and 2B are perspective views of a base unit of the cardiac event monitoring system of FIG. 1.
Figure 2B:
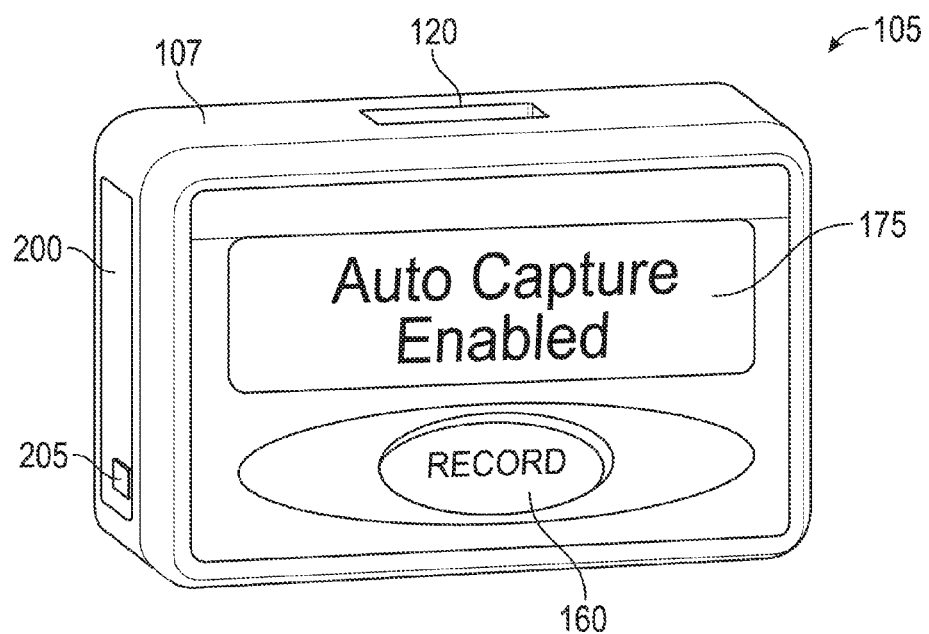

Referring also to FIGS. 2A and 2B, the base unit 105 is pager-sized, and is either handheld or patient-worn. The base unit 105 includes the body 107 that houses components that control operation of the system 100. Thus, the base unit 105 includes a controller 150 within the body 107, and various input and output devices coupled to the controller 150 through the body 107. The controller 150 receives power from a power source 155 that may be provided by batteries that are placed within a compartment 200 on a side of the body 107. The body 107 and the battery compartment 200 can be made of a suitable non-conductive lightweight material, such as a rigid plastic.

The controller 150 includes a processor 151, memory 152, a clock 153, and a counter 154 to process signals from the wearable electrode system 110 and/or the plug-in adapter 115, receive input from a patient or a service technician using the system 100, and transmit recorded data to a monitoring center, as provided by a health professional, a clinic, or a hospital. The input devices on the base unit 105 include a symptom record button 160, a yes/transmit button 165, and a no button 170. The yes/transmit button 165 can be used in one of two ways: it can be used as a response button to answer "yes" when queried by the controller 150, or it can be used to indicate to the controller 150 to transmit the ECG. The no button 170 can be used in one of two ways: it can be used as a response button to answer "no" when queried by the controller 150, it can be used to indicate to the controller 150 to cancel a transmission of an ECG.

The output devices on the base unit 105 include a display 175 such as a liquid crystal display (LCD) that provides an interface with the patient and/or a technician, and a speaker 180 for transmitting data regarding the recording.

The system 100 is designed to record, store, and transmit ambulatory ECG signals received from the wearable electrode system 110 or the plug-in adapter 115. The system 100 can be worn for days or weeks, as it is intended for use by patients who are experiencing symptoms that are transient and infrequent in nature. The base unit 105 can be worn outside the patient's clothing if there is any chance that moisture (for example, sweat) might come in contact with the base unit 105. The base unit 105 can be worn under outer wear, such as raincoats or jackets, for protection during wet or cold conditions.

A patient would normally operate the base unit 105 and the wearable electrode system 110 as a single unit to capture ECG data. However, some patients who want the features of the base unit 105 and the wearable electrode system 110 may also want the option of finger electrode capture, which is less irritating to the patient than using the wearable electrodes 130, which have to be placed on the patient's skin to obtain data. Thus, the plug-in adapter 115 is designed to couple with the base unit 105 when the wearable electrode system 110 is disconnected or detached from the base unit 105.

Referring to FIGS. 3A-3D, the plug-in adapter 115 includes a housing 300 having finger electrodes 305, 310 on one side of the housing 300 and an adapter connector 315 protruding from another side of the housing 300. The electrodes 305, 310 are positioned such that, when the adapter 115 is attached to the base unit 105, a patient may easily place the surface of a finger on each of the electrodes 305, 310 while holding the base unit 105. The fingers used by the patient may be any of the five terminating members of the patient's hand. The adapter connector 315 is configured to plug into the base connector 120 and the connections within the connector 315 are the same as those of the connector 135 of the wearable electrode system 110 to enable both the adapter 115 and the wearable electrode system 110 to be used with the base unit 105. The housing 300 is made of a lightweight non-conductive material such as a rigid plastic. The adapter 115 is generally sized to be smaller than the base unit 105 but large enough to accommodate the fingers at the electrodes 305, 310. The adapter 115 can be rectangular in shape, as shown in the drawings.

Figure 3A:
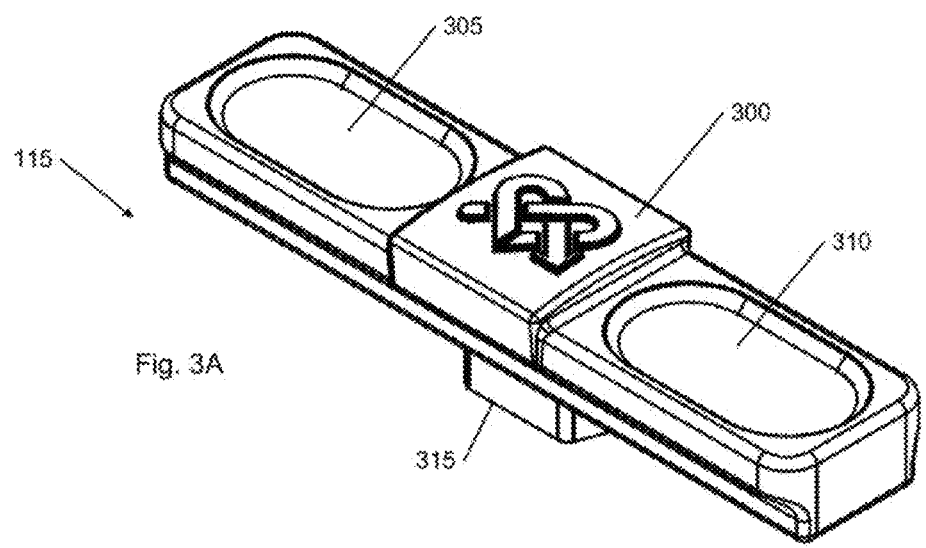
FIG. 3A is a perspective view of a plug-in adapter of the cardiac event monitoring system of FIG. 1.
Figure 3B:
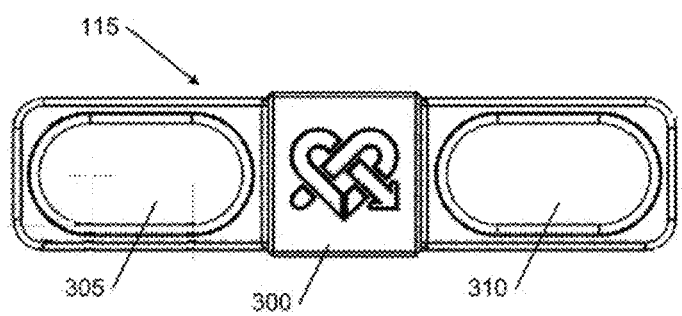
FIGS. 3B-3D are top, front, and side plan views of the plug-in adapter of FIG. 3A.
Figure 3C:
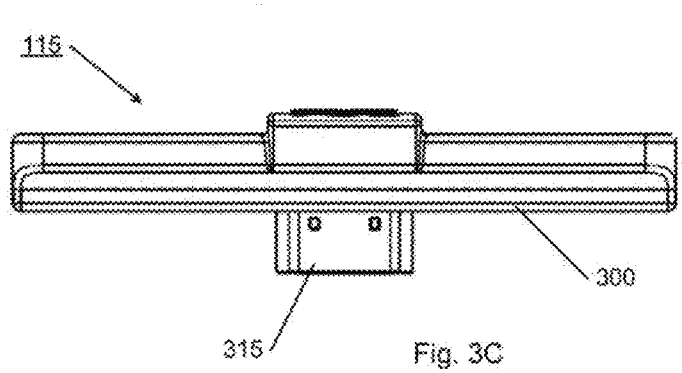
Figure 3D:
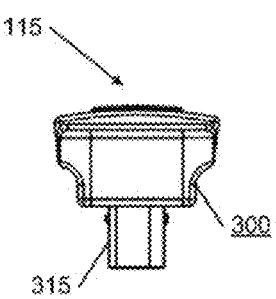
Figure 3E:
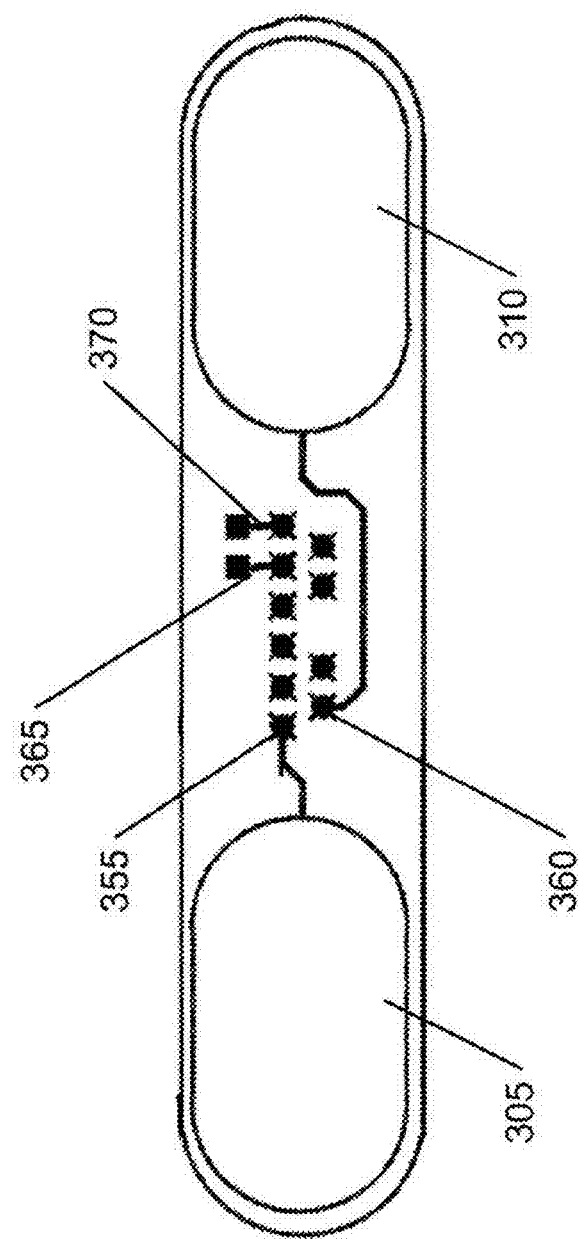
FIG. 3E is an electrical diagram of the plug-in adapter of FIG. 3A.

Referring also to FIG. 3E, the adapter 115 includes electrical connections 355, 360 from the electrodes 305, 310 to the adapter connector 315. The electrical connections 355, 360 connect to the controller 150 of the base unit 105 in the same fashion as the electrical connections within the wearable electrode system 110. Additionally, the adapter 115 includes a unique identifier that enables the base unit 105 to identify the adapter 115 when it is connected to the base unit 105. For example, the unique identifier can be formed from an internal resistance formed by resistors 365, 370 having a value unique to the adapter 115.

Figure 4:
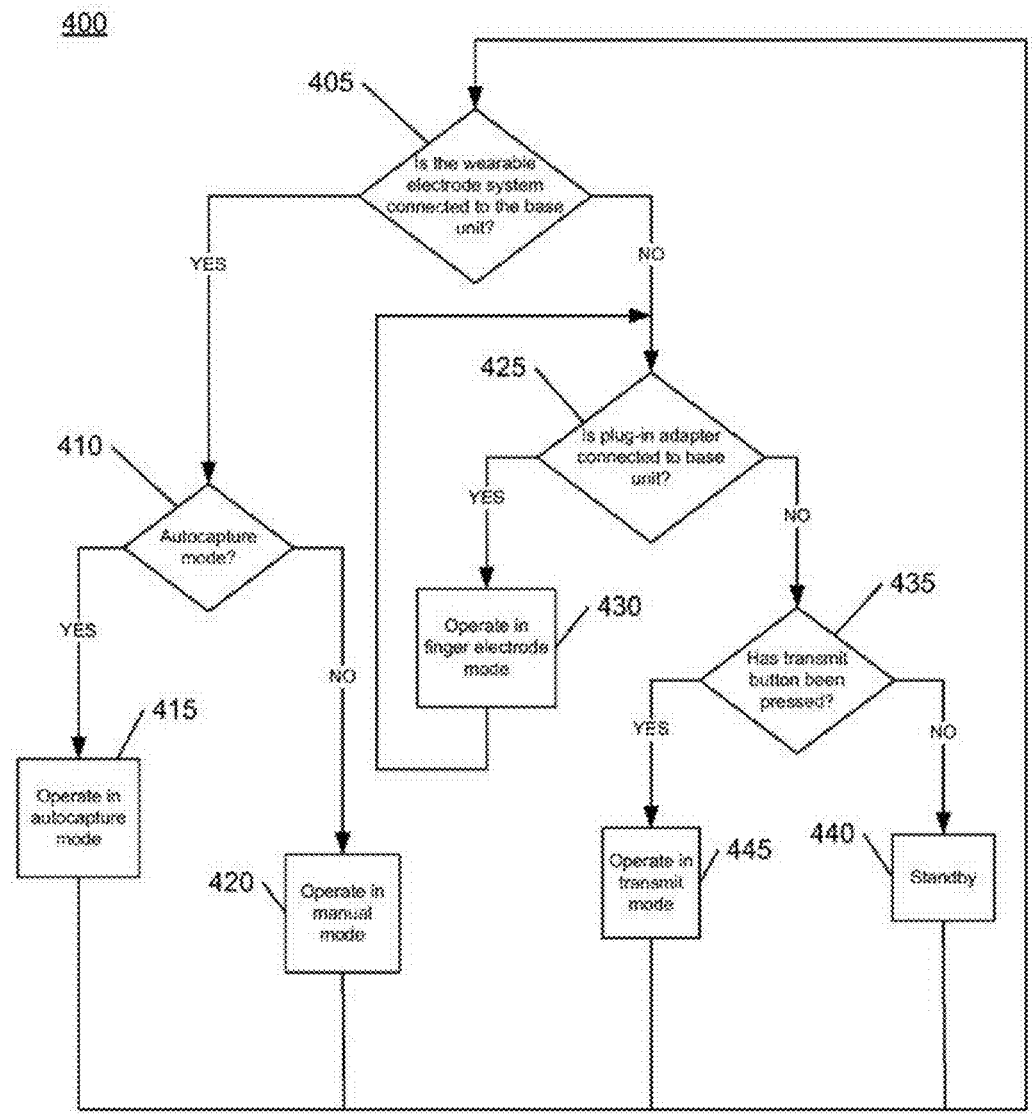
FIG. 4 is a flow chart of a procedure describing operation of the cardiac event monitoring system of FIG. 1.

Referring also to FIG. 4, a procedure 400 is performed by the cardiac event monitoring system 100 for monitoring cardiac events of a patient. In general the base unit 105 turns off after a period of inactivity to conserve energy of the power source 155. The base unit 105 can be set up so that the patient can turn on the base unit 105 by pressing any button on the base unit 105. Initially, the controller 150 determines whether the wearable electrode system 110 is connected to the base unit 105 (step 405). For example, the wearable electrode system 110 could be equipped with an internal resistance that is unique to the wearable electrode system 110, and the base unit 105 could detect the resistance when the wearable electrode system 110 is connected to the base unit 105. If the wearable electrode system 110 is connected to the base unit 105, then the controller 150 determines if the patient had set up the base unit 105 to operate in auto capture mode by, for example, selecting auto capture mode during a set up operation (step 410). If the patient had pre-selected the auto capture mode (step 410), then the controller 150 operates in the auto capture mode (step 415), a mode in which the controller 150 determines when to record the ECG, without the input from the patient.

During the auto capture mode (step 415), the patient carries the small, battery-powered system 100 on their person for the duration of the testing period. The electrodes 130 are attached to the patient's body, such as, for example, the patient's chest, using the associated adhesive patches, and the electrodes 130 detect the electrical signals from the patient's heart. The controller 150 continuously analyzes the signals from the electrodes 130 to detect an abnormality in the electrical signal of the heart. If the controller 150 detects an abnormality, the controller 150 records and stores the event data according to pre-defined protocols. Moreover, any memory 152 that is devoted to the auto capture mode can be dynamically managed and overwritten, as needed, for new activity. Moreover, the controller 150 can send a signal to the speaker 180 indicating to the patient that data has been recorded and that the patient should transmit that data to a monitoring center. The controller 150 operates in auto capture mode (step 415) until it receives an indication that the wearable electrode system 110 is disconnected from the base unit 105 (step 405) or unless the patient had set up the base unit 105 to operate in manual mode (step 410).

If the controller 150 determines that the wearable electrode system 110 is connected to the base unit 105 (step 405) and the patient set up the base unit 105 to operate in manual mode (step 410), then the controller 150 operates in a manual mode (step 420). As with the auto capture mode, the patient carries the battery-powered system 100 on their person for the duration of the testing period in the manual mode. The electrodes 130 are attached to the patient's body and the electrodes 130 detect the electrical signals from the patient's heart. When a symptom occurs, the patient triggers the controller 150 in the base unit 105 to record the ECG by pressing the symptom record button 160. The display 175 shows a countdown message while the recording takes place. The controller 150 operates in manual mode (step 420) until it receives an indication that the wearable electrode system 110 is disconnected from the base unit 105 (step 405) or unless the patient sets up the base unit 105 to operate in auto capture mode (step 410).

Figure 5:
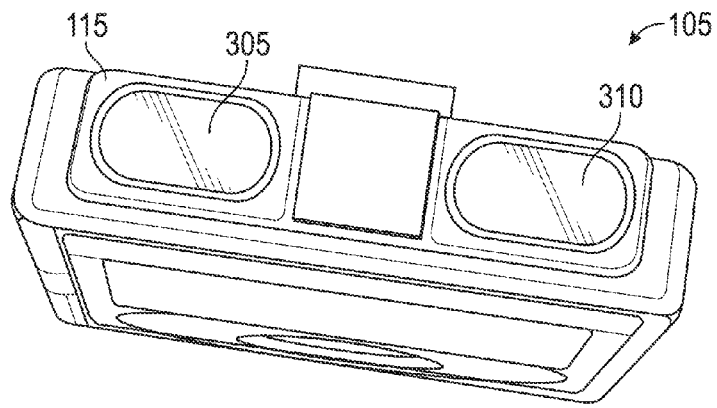
FIG. 5 is a perspective view showing the cardiac event monitoring system of FIG. 1 with the plug-in adapter of FIG. 3A connected to the base unit of FIGS. 2A and 2B.

If the controller 150 determines that the wearable electrode system 110 is not connected to the base unit 105 (step 405), then the controller 150 determines whether the plug-in adapter 115 is connected to the base unit 105 (step 425). For example, the plug-in adapter 115 could be equipped with the resistors 365, 370 having a resistance that is unique to the plug-in adapter, and the base unit 105 could detect the resistance when the plug-in adapter 115 is connected to the base unit 105. If the plug-in adapter 115 is connected to the base unit 105, as shown in FIG. 5, then the controller 150 operates in the finger electrode mode (step 430). During the finger electrode mode (step 430), the base unit 105 shuts off or operates in a standby mode, and the controller 150 can maintain the display 175 on standby to conserve power in the power source 155 until the patient takes an action to initiate a data recording.

Figure 6:
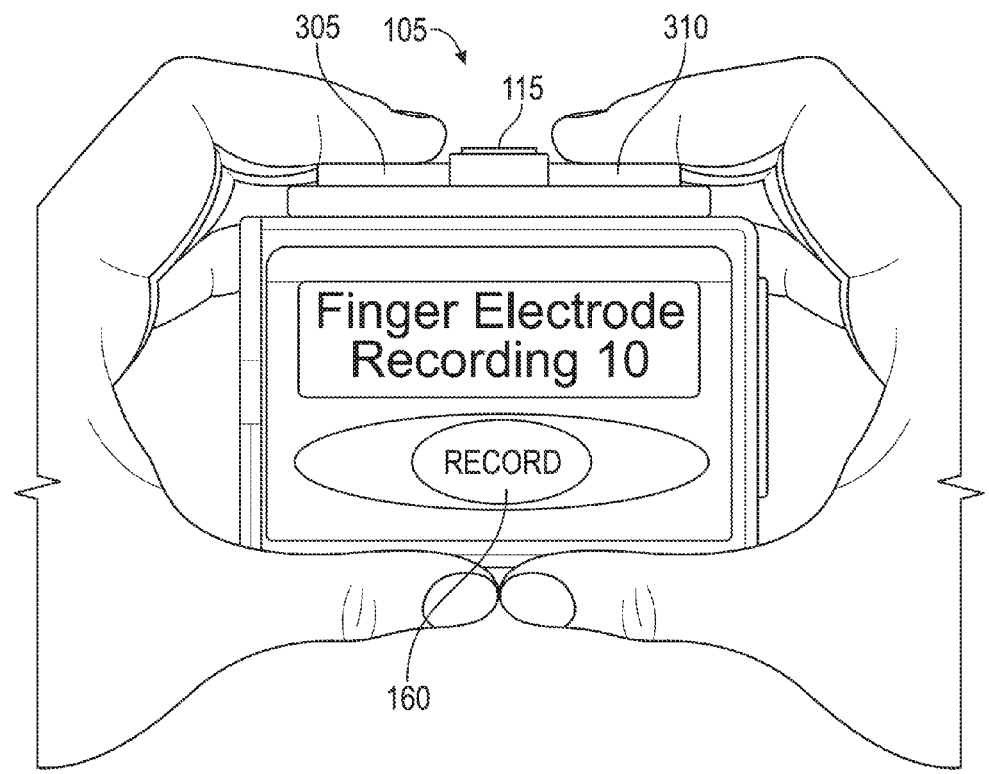
FIG. 6 is a perspective view showing a patient using the cardiac event monitoring system of FIG. 1 with the plug-in adapter of FIG. 3A connected to the base unit of FIGS. 2A and 2B.

When the patient experiences a symptom, he presses the symptom record button 160 and watches the display 175, as shown in FIG. 6. The controller 150 determines that the button 160 has been pressed and enters a countdown mode, sending signals to the display 175 to display a "countdown to record" message that instructs the patient to place the fingers on the electrodes 305, 310 such that the electrodes 305, 310 make contact with the fingers. After the controller 150 has completed counting down, the countdown mode ends, and the controller 150 causes the display 175 to display an indication that the base unit 105 is recording data. For example, the display 175 can display the message "Finger Electrode Recording XX", where XX is the number of seconds that were specified as a measurement duration during setup of the base unit 105. For example, as shown in FIG. 6, the display message is "Finger Electrode recording 10." The controller 150 counts down to zero from the XX value, and, upon reaching zero, the controller 150 enters a transmit prompt mode. The controller 150 can send a signal to the display 175 to display a message requesting that the patient transmit the recorded signal, as discussed below. The controller 150 operates in finger electrode mode (step 430) until it receives an indication that the plug-in adapter 115 is disconnected from the base unit 105 (step 425).

After the recording is complete, the patient disconnects either the wearable electrode system 110 or the plug-in adapter 115 from the base unit 105. Therefore, the controller 150 determines that the wearable electrode system 110 is not connected to the base unit 105 (step 405) and the plug-in adapter 115 is not connected to the base unit 105 (step 425). The controller 150 then determines if the yes/transmit button 165 has been pressed (step 435). In this implementation, the base unit 105 is configured to only transmit if both the wearable electrode system 110 and the plug-in adapter 115 are disconnected from the base unit 105. If the yes/transmit button 165 has not been pressed (step 435), then the controller 150 causes the base unit 105 to enter into standby mode to conserve energy (step 440).

If the controller 150 determines that the yes/transmit button 165 has been pressed (step 435), then the controller 150 operates in transmit mode (step 445). During transmit mode, the patient transmits the ECG data to a monitoring center using a telephone or some other suitable device. To transmit the ECG data, the patient calls the monitoring center, and follows the directions given by the monitoring center. Next, the patient places the base unit 105 on a flat surface near the telephone and places the mouthpiece of the phone behind the base unit 105. The patient presses the yes/transmit button 165, which indicates to the controller 150 to send a signal to the speaker 180 to start transmission of the ECG data. During transmission, the speaker 180 emits a series of tones that indicate the ECG data. If needed, in some circumstances, the patient can re-transmit ECG data.

The monitoring center staff reviews the tracings and, when necessary, notifies the patient's physician immediately. A report is generated and forwarded to the physician. In the implementation shown in FIG. 4, the patient removes the cable connector 135 of the wearable electrode system 110 and the plug-in adapter 115 from the base unit 105 prior to transmission.

Other implementations are within the scope of the following claims. For example, in other implementations, the base unit 105 could be configured to be able to transmit when either the wearable electrode system 110 or the plug-in adapter 115 is connected from the base unit 105. Thus, in this implementation, the patient is not required to remove the wearable electrode system 110 or the plug-in adapter 115 from the base unit 105 prior to transmitting the data. The patient may merely be required to press the transmit button 165 in order to initiate the transmit mode.

The base unit 105 can be any size suitable for permitting a patient to carry the base unit 105 on the patient's body without undue hardship.

Alternatively, the patient can wait to transmit the ECG data, which can be stored within the memory 152 of the controller 150, for a period of time after the data is recorded.

The plug-in adapter 115 can be formed from other suitable shapes, or can be ergonomically designed. For example, the adapter 115 can have a flat base that faces the base unit 105 when plugged into the base unit 105 and have a triangularly-shaped outer surface with two angled surfaces such that the electrodes 305, 310 are formed along the angled surfaces. As another example, the adapter 115 can have a flat base that faces the base unit 105 when plugged into the base unit 105 and have a concave or convex outer surface on which the electrodes 305, 310 are formed. The outer surface can be polygonal, with each side including an electrode. Although the plug-in adapter 115 is suitable for making contact between the patient's fingers and the electrodes 305, 310, the plug-in adapter 115, and, in particular, the electrodes 305, 310, can be contacted to any body part of the patient. For example, the electrodes 305, 310 can be contacted to the chest, the legs, or the arms of the patient. Moreover, the electrodes 305, 310 may be designed with different shapes or sizes.

The power source 155 may be turned off and on by a switch 205 (FIGS. 1 and 2B) accessible on the compartment 200 and connected to the power source 155 and the controller 150

Some of the illustrative aspects of the present invention may be advantageous in solving the problems herein described and other problems not discussed which are discoverable by a skilled artisan.

While the above description contains much specificity, these should not be construed as limitations on the scope of any embodiment, but as exemplifications of the presented embodiments thereof. Many other ramifications and variations are possible within the teachings of the various embodiments. While the invention has been described with reference to exemplary embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best or only mode contemplated for carrying out this invention, but that the invention will include all embodiments falling within the scope of the appended claims. Also, in the drawings and the description, there have been disclosed exemplary embodiments of the invention and, although specific terms may have been employed, they are unless otherwise stated used in a generic and descriptive sense only and not for purposes of limitation, the scope of the invention therefore not being so limited. Moreover, the use of the terms first, second, etc. do not denote any order or importance, but rather the terms first, second, etc. are used to distinguish one element from another. Furthermore, the use of the terms a, an, etc. do not denote a limitation of quantity, but rather denote the presence of at least one of the referenced item.

Thus the scope of the invention should be determined by the appended claims and their legal equivalents, and not by the examples given.

That which is claimed is:

1. A cardiac event monitoring system comprising:
a base unit comprising:
a base connector, and
a controller,
wherein the controller comprises a processor and a memory; and
a plug-in adapter comprising:
a housing,
a plurality of electrodes including first and second electrodes each positioned on a first side of the housing and each configured to detect electrical signals from a heart of a patient when the first electrode is contacted by a first finger of the patient and the second electrode is contacted by a second finger of the patient, and
an adapter connector positioned on a second side of the housing substantially opposite the first side and configured to removably couple with the base connector;
wherein, upon electrical coupling of the adapter connector of the plug-in adapter to the base connector of the base unit, the processor is configured to receive the electrical signals from the first and second electrodes and to store the electrical signals as electrocardiogram (ECG) data to the memory.

2. The cardiac event monitoring system according to claim 1 wherein the plurality of electrodes of the plug-in adapter consists of the first and second electrodes.

3. The cardiac event monitoring system according to claim 1 wherein each of the first and second electrodes of the plug-in adapter is sized to receive a respective finger of the patient.

4. The cardiac event monitoring system according to claim 1 wherein the plurality of electrodes of the plug-in adapter further comprises a third electrode configured to couple with a respective body part of the patient and to detect the electrical signals.

5. The cardiac event monitoring system according to claim 1 wherein the controller is further configured to operate in a finger electrode mode.

6. The cardiac event monitoring system according to claim 1 wherein the base unit comprises a speaker configured to emit audible tones representing a portion of the ECG data retrieved from the memory.

7. The cardiac event monitoring system according to claim 1 wherein the base unit comprises a display configured to display the ECG data retrieved by the processor from the memory.

8. The cardiac event monitoring system according to claim 1 wherein the base unit comprises one or more input devices electrically coupled to the controller and comprising at least one of a symptom record button, a yes/transmit button, and a no/cancel button.

9. The cardiac event monitoring system according to claim 1 wherein the base unit and the plug-in adapter, in combination, are handheld-sized.

10. The cardiac event monitoring system according to claim 1 wherein the controller is configured to transmit the ECG data to a monitoring center.

11. The cardiac event monitoring system according to claim 10 wherein each of the plurality of electrodes is sized to receive a respective finger of the patient.

12. The cardiac event monitoring system according to claim 10 wherein two or more of the plurality of electrodes of the plug-in adapter are configured to couple with a respective body part of the patient and to detect the electrical signals.

13. The cardiac event monitoring system according to claim 10 wherein the base unit comprises one or more input devices electrically coupled to the controller and configured to selectively initiate recording of the ECG data to the memory, to start transmission of the ECG data to the monitoring center, and to stop transmission of the ECG data to the monitoring center.

14. A method of monitoring cardiac events generated as electrical signals using a base unit comprising a base connector and a controller characterized by a processor and a memory, and using a plug-in adapter comprising a housing, a plurality of electrodes including first and second electrodes each positioned on a first side of the housing, and an adapter connector positioned on a second side of the housing substantially opposite the first side and configured to removably couple with the base connector, the method comprising:
electrically coupling the adapter connector of the plug-in adapter to the base connector of the base unit;
detecting, using the plurality of electrodes, the electrical signals from a heart of a patient when the first electrode is contacted by a first finger of the patient and the second electrode is contacted by a second finger of the patient; and
operating the processor of the controller to receive the electrical signals fro he plurality of electrodes of the plug-in adapter.

15. The method according to claim 14 wherein the plurality of electrodes further comprises a third electrode; wherein the method further comprises the step of operating the processor of the controller to receive the electrical signals from the third electrode of the plug-in adapter when a body part of the patient makes contact with the third electrode.

16. The method according to claim 14 further comprising operating the processor of the controller to transmit the electrical signals to a monitoring center.

17. The method according to claim 16 further comprising storing electrocardiogram (ECG) data in a memory that represents the electrical signals received from the plug-in adapter for a time period or until the ECG data are transmitted to the monitoring center.

18. The method according to claim 14 further comprising displaying instructions to the patient on a display carried by the base unit.

19. The method according to claim 18 further comprising receiving instructions from the patient from one or more input devices carried by the base unit.

* * * * *